US00PP23271P2

(12) United States Plant Patent
van den Hoogen

(10) Patent No.: US PP23,271 P2
(45) Date of Patent: Dec. 25, 2012

(54) ***VERONICA* PLANT NAMED 'ALLLADY'**

(50) Latin Name: *Veronica longifolia*
Varietal Denomination: Alllady

(75) Inventor: Wilhelmus T. J. van den Hoogen, Cuijk (NL)

(73) Assignee: Allplants Holding B.V., Cuijk (NL)

( * ) Notice: Subject to any disclaimer, the term of this patent is extended or adjusted under 35 U.S.C. 154(b) by 0 days.

(21) Appl. No.: 13/199,169

(22) Filed: Aug. 22, 2011

(51) Int. Cl.
*A01H 5/00* (2006.01)

(52) U.S. Cl. ..... Plt./251

(58) Field of Classification Search ..... Plt./251
See application file for complete search history.

*Primary Examiner* — Kent L Bell
(74) *Attorney, Agent, or Firm* — C. A. Whealy

(57) ABSTRACT

A new and distinct cultivar of *Veronica* plant named 'Alllady', characterized by its upright plant habit; freely flowering habit; compact and dense inflorescences with numerous white-colored flowers; long flowering period; and potential to be used as a cut flower or as a container plant.

3 Drawing Sheets

Botanical designation: *Veronica longifolia.*
Cultivar denomination: 'ALLLADY'.

BACKGROUND OF THE INVENTION

The present invention relates to a new and distinct cultivar of *Veronica* plant, botanically known as *Veronica longifolia* and hereinafter referred to by the name 'Alllady'.

The new *Veronica* plant is a product of a planned breeding program conducted by the Inventor in Cuijk, The Netherlands. The objective of the breeding program is to create new attractive *Veronica* plants that can be used as either a cut flower or as a container plant.

The new *Veronica* plant originated from an open-pollination in September, 2007 of a proprietary selection of *Veronica longifolia* identified as code number N6-28, not patented, as the female, or seed, parent with an unknown selection of *Veronica longifolia* as the male, or pollen, parent. The new *Veronica* plant was discovered and selected by the Inventor as a single flowering plant from within the progeny of the stated open-pollination in a controlled environment in Cuijk, The Netherlands in August, 2009.

Asexual reproduction of the new *Veronica* plant by vegetative cuttings in a controlled environment in Cuijk, The Netherlands, since September, 2009, has shown that the unique features of this new *Veronica* plant are stable and reproduced true to type in successive generations.

SUMMARY OF THE INVENTION

Plants of the new *Veronica* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Alllady'. These characteristics in combination distinguish 'Alllady' as a new and distinct *Veronica* plant:

1. Upright plant habit.
2. Freely flowering habit.

3. Compact and dense inflorescences with numerous white-colored flowers.
4. Long flowering period.
5. Can be used as a cut flower or as a container plant.

Plants of the new *Veronica* differ primarily from plants of the female parent selection in the following characteristics:

1. Plants of the new *Veronica* are more compact than plants of the female parent selection.
2. Plants of the new *Veronica* are more freely branching than plants of the female parent selection.

Plants of the new *Veronica* can be compared to plants of *Veronica longifolia* 'Alllove', disclosed in U.S. Plant Pat. No. 21,478. In side-by-side comparisons conducted in Cuijk, The Netherlands, plants of the new *Veronica* differed primarily from plants of 'Alllove' in the following characteristics:

1. Plants of the new *Veronica* had narrower leaves than plants of 'Alllove'.
2. Plants of the new *Veronica* and 'Alllove' differed in flower color as plants of 'Alllove' had red purple-colored flowers.
3. Flowers of plants of the new *Veronica* did not develop stamens whereas flower of plants of 'Alllove' developed stamens.

BRIEF DESCRIPTION OF THE PHOTOGRAPHS

The accompanying colored photographs illustrate the overall appearance of the *Veronica* plant showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Alllady' grown in a 13-cm container.

The photograph on the second sheet is a close-up view of typical inflorescences of 'Alllady'.

The photograph on the third sheet is a close-up view of a typical leaf of 'Alllady'.

DETAILED BOTANICAL DESCRIPTION

Plants used for the aforementioned photographs and following description were grown during the spring and early summer in an outdoor nursery in Cuijk, The Netherlands and under environmental conditions and cultural practices which closely approximate commercial production. During the production of the plants, day temperatures ranged from 12° C. to 28° C. and night temperatures ranged from 4° C. to averaged 18° C. Plants were 14 months old when the photographs and the description were taken. In the following description, color references are made to The Royal Horticultural Society Colour Chart, 2007 Edition, except where general terms of ordinary dictionary significance are used.

Botanical classification: *Veronica longifolia* 'Alllady'.

Parentage:

*Female, or seed, parent*.—Proprietary selection of *Veronica longifolia* identified as code number N6-28, not patented.

*Male, or pollen, parent*.—Unknown selection of *Veronica longifolia*, not patented.

Propagation:

*Type cutting*.—Vegetative cuttings.

*Time to initiate roots*.—About 10 to 14 days at 12° C. to 30° C.

*Time to produce a rooted young plant*.—About 24 to 32 days at 12° C. to 30° C.

*Root description*.—Fine, fleshy; white in color.

*Rooting habit*.—Freely branching; dense.

Plant description:

*Plant type*.—Herbaceous perennial.

*Plant and growth habit*.—Upright inverted triangle; freely basal branching habit with about 20 main stems; moderately vigorous growth habit.

*Plant height*.—About 59 cm.

*Plant width*.—About 53.5 cm.

*Lateral branch description*.—Length: About 46.6 cm. Diameter: About 5 mm. Internode length: About 4.9 cm. Strength: Strong. Texture: Sparsely pubescent. Color: Close to 144B.

Foliage description:

*Arrangement*.—Opposite, simple.

*Length*.—About 8.4 cm.

*Width*.—About 2.1 cm.

*Shape*.—Lanceolate.

*Apex*.—Acute.

*Base*.—Attenuate.

*Margin*.—Serrate.

*Texture, upper surface*.—Smooth, glabrous.

*Texture, lower surface*.—Mostly smooth and glabrous however, along main vein, sparsely pubescent.

*Venation pattern*.—Pinnate.

*Color*.—Developing leaves, upper surface: Close to 137A to 137B. Developing leaves, lower surface: Close to 137D. Fully expanded leaves, upper surface: Close to N137A to N137B; venation, close to 144A. Fully expanded leaves, lower surface: Between 138B and 146B; venation, close to 144B.

*Petiole length*.—About 1.1 cm.

*Petiole diameter*.—About 2 mm by 2.5 mm.

*Petiole texture, upper and lower surfaces*.—Smooth, glabrous.

*Petiole color, upper and lower surfaces*.—Close to 144C.

Flower description:

*Flower arrangement and shape*.—Single campanulate flowers arranged on primary and secondary terminal racemes; racemes compact and dense; flowers face mostly outwardly.

*Flowering habit*.—Freely flowering, each terminal branch has one primary raceme and about nine secondary racemes; about 235 flowers per primary inflorescence and about 140 flowers per secondary inflorescence.

*Fragrance*.—None detected.

*Natural flowering season*.—Plants begin flowering about seven weeks after pinching; flowering continuous from July to late September in The Netherlands.

*Flower longevity on the plant*.—About one week; flowers not persistent.

*Flower buds*.—Length: About 4 mm. Diameter: About 2 mm. Shape: Obovate. Color: Close to NN155D; calyx, close to 137C.

*Inflorescence height*.—About 9.5 cm.

*Inflorescence diameter*.—About 1.7 cm.

*Flower diameter*.—About 4 mm.

*Flower height*.—About 6 mm.

*Petals*.—Quantity and arrangement: About four in a single whorl, petals fused about 50% of the length from the base. Length: About 5 mm. Width: About 2 mm. Shape: Obovate. Apex: Obtuse. Margin: Entire. Texture, upper surface: Mostly smooth and glabrous; towards the base, moderately pubescent. Texture, lower surface: Smooth, glabrous. Color: When opening, upper and lower surfaces: Close to NN155D. Fully opened, upper and lower surfaces: Close to NN155D.

*Sepals*.—Quantity and arrangement: About four in a single whorl, sepals fused about 5% of the length from the base. Length: About 2.5 mm. Width: About 1 mm. Shape: Ovate. Apex: Acute. Margin: Entire. Texture, upper and lower surfaces: Smooth, glabrous. Color: When opening, upper and lower surfaces: Close to 144A to 144B. Fully opened, upper and lower surfaces: Close to 144A to 144B.

*Peduncles*.—Length: About 14.9 cm. Diameter: About 3 mm. Aspect: Primary racemes, mostly upright; secondary racemes, about 25° from vertical. Strength: Strong. Texture: Smooth, glabrous. Color: Close to 143B to 143C.

*Pedicels*.—Length: About 1 mm. Diameter: About 0.5 mm. Aspect: About 60° from peduncle axis. Strength: Moderately strong. Texture: Smooth, glabrous. Color: Close to 144B.

*Reproductive organs*.—Stamens: Stamen development has not been observed on plants of the new *Veronica*. Pistils: Quantity per flower: One. Pistil length: About 3 mm. Stigma shape: Clavate. Stigma color: Close to 145D. Style length: About 2.7 mm. Style color: Close to 157A. Ovary color: Close to 143B.

*Seeds and fruits*.—Seed and fruit development has not been observed on plants of the new *Veronica*.

Disease & pest resistance: Plants of the new *Veronica* have not been noted to be resistant to pathogens and pests common to *Veronica*.

Garden performance: Plants of the new *Veronica* have exhibited good garden performance and to be tolerant to rain, wind, high temperatures of about 35° C. and to be hardy to USDA Hardiness Zone 4.

It is claimed:

1. A new and distinct *Veronica* plant named 'Alllady' as illustrated and described.

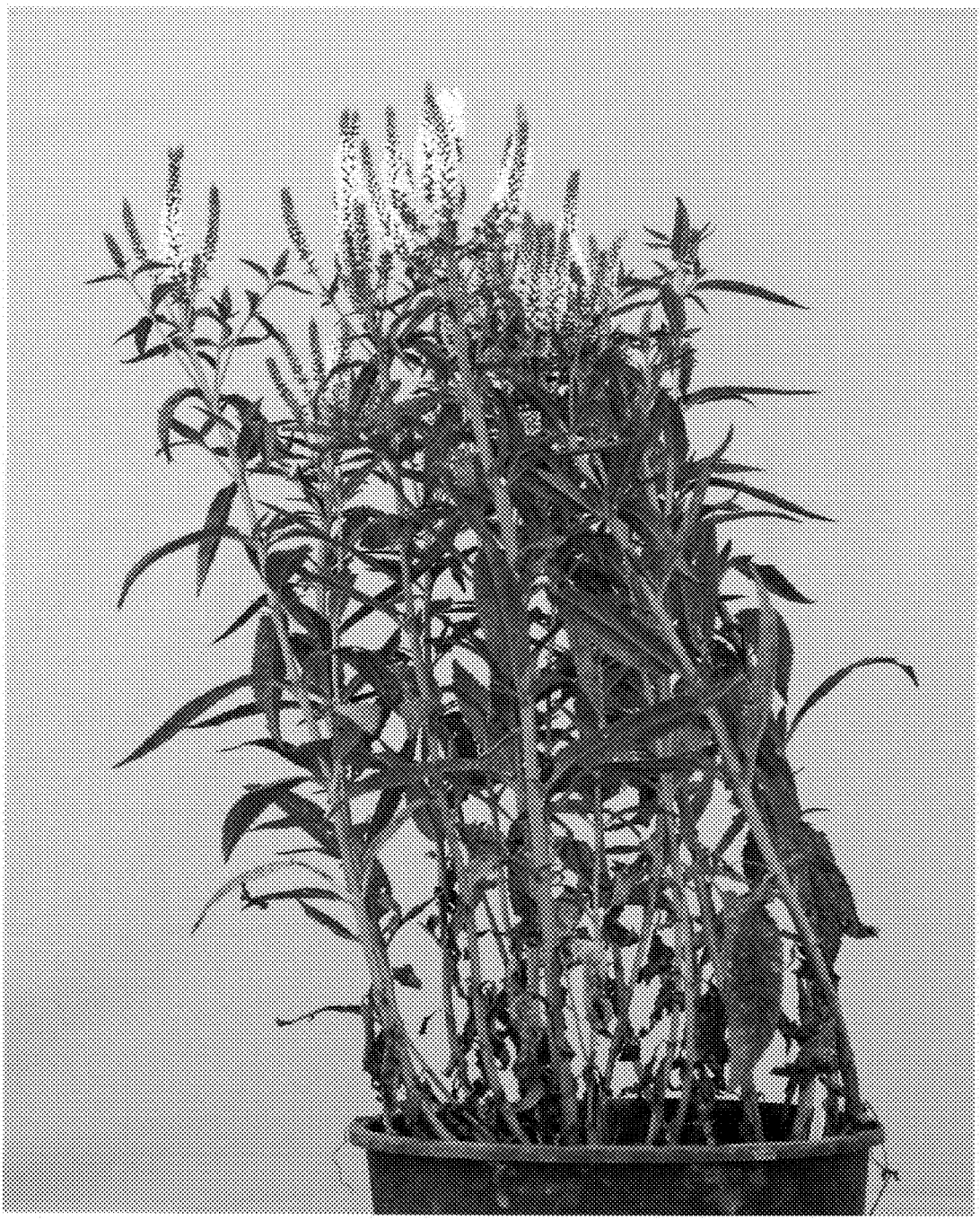

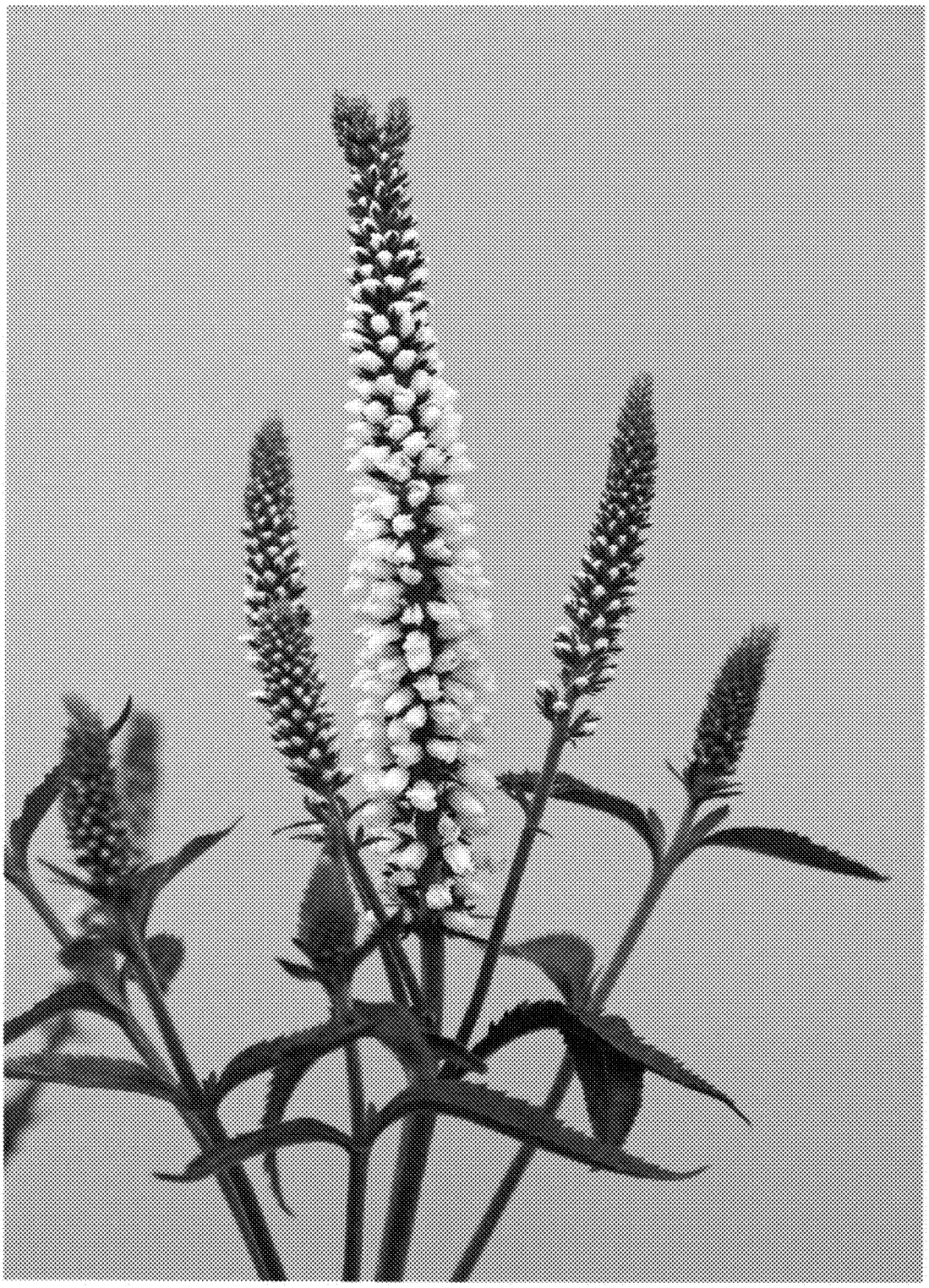

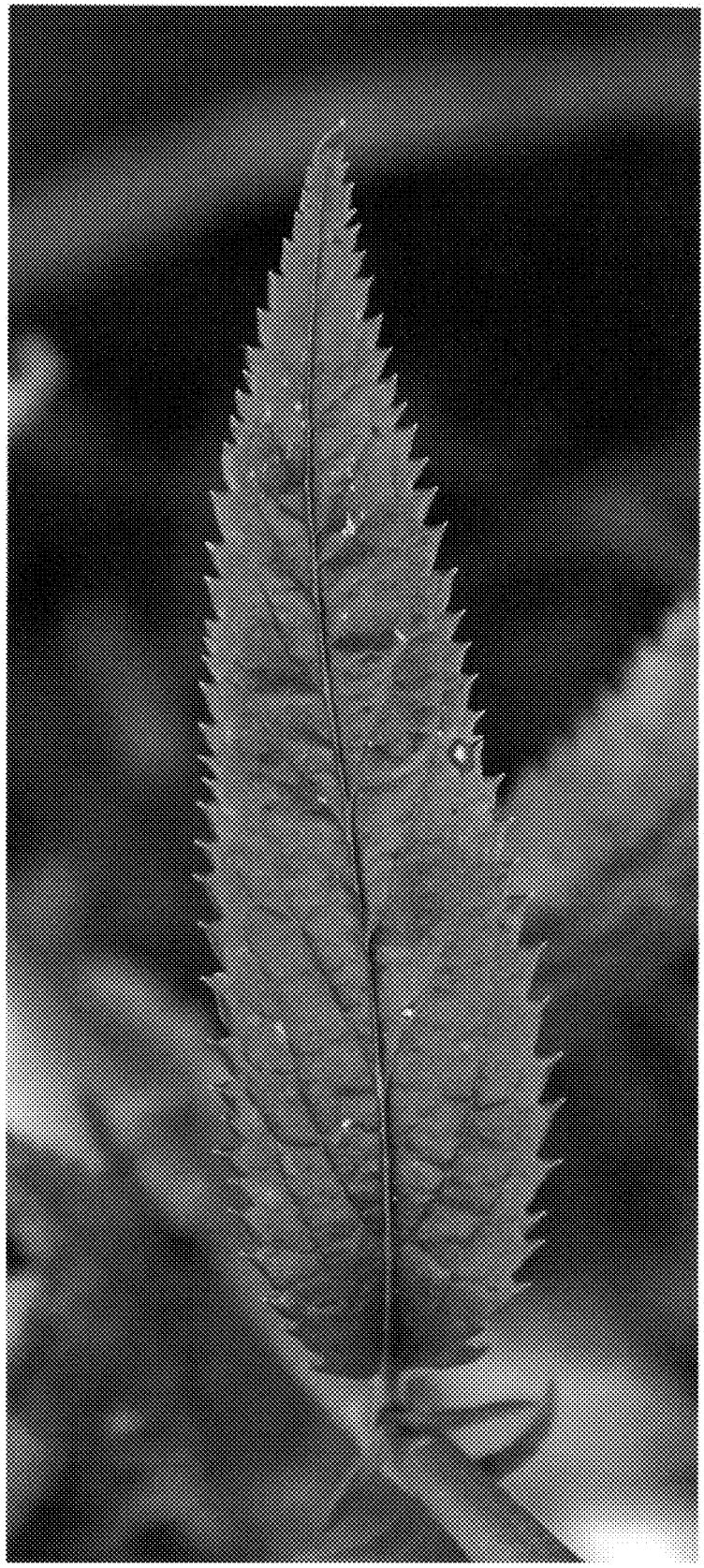

* * * * *